United States Patent
Magee (10) Patent No.: US 8,545,406 B2
(45) Date of Patent: Oct. 1, 2013

(54) DYNAMIC APERTURE CONTROL AND NORMALIZATION FOR APODIZATION IN BEAMFORMING

(75) Inventor: David Patrick Magee, Allen, TX (US)

(73) Assignee: Texas Instruments Incorporated, Dallas, TX (US)

( * ) Notice: Subject to any disclaimer, the term of this patent is extended or adjusted under 35 U.S.C. 154(b) by 0 days.

(21) Appl. No.: 13/305,378

(22) Filed: Nov. 28, 2011

(65) Prior Publication Data
US 2012/0143059 A1 Jun. 7, 2012

Related U.S. Application Data

(60) Provisional application No. 61/420,068, filed on Dec. 6, 2010.

(51) Int. Cl.
*A61B 8/00* (2006.01)

(52) U.S. Cl.
USPC ............ 600/437; 600/407; 600/443; 600/447

(58) Field of Classification Search
USPC ................... 600/407, 437, 443, 447
See application file for complete search history.

(56) References Cited

U.S. PATENT DOCUMENTS

| | | | |
|---|---|---|---|
| 4,180,790 A | 12/1979 | Thomas | |
| 5,647,365 A | 7/1997 | Abboud | |
| 6,436,044 B1 * | 8/2002 | Wang | 600/443 |
| 2006/0173313 A1 | 8/2006 | Lui et al. | |
| 2009/0326375 A1 | 12/2009 | Magee | |

* cited by examiner

*Primary Examiner* — Tse Chen
*Assistant Examiner* — Jason Ip
(74) *Attorney, Agent, or Firm* — Alan A. R. Cooper; W. James Brady, III; Frederick J. Telecky, Jr.

(57) ABSTRACT

A method of apodizing for ultrasound beamforming includes providing filtered digital channel data representing echo data from target tissue in a plurality (k) of data channels and a predefined number of active channels ($N_{act}$). A software-based integrated apodization algorithm dynamically apodizes the digital channel data using a selected apodizing function h[n,k], n being the sample number. The integrated apodization algorithm applies dynamic aperture control to create an effective aperture by generating a parameter numApertureChannels ($N_{ap}[n]$), where $N_{ap}[n] \leq N_{act}$, and selecting $N_{ap}[n]$ particular data channels based on a dynamic beam focusing location for beamforming. Applied dynamic data scaling provides data normalization using a vector inner product between h[n,k] and a scale factor to generate normalized apodization factors $h_{norm}[n,k]$. The normalized apodization factors are applied to the digital channel data in the $N_{ap}[n]$ particular data channels to generate apodized and normalized digital channel data.

13 Claims, 5 Drawing Sheets

METHOD 500

501 — PROVIDING DIGITAL CHANNEL DATA REPRESENTING ECHO DATA RECEIVED FROM TARGET TISSUE IN EACH OF A PLURALITY (k) OF DATA CHANNELS, AND A PREDEFINED NUMBER OF ACTIVE DATA CHANNELS (Nact) SELECTED FROM THE PLURALITY OF DATA CHANNELS 502 — APPLYING A SOFTWARE-BASED INTEGRATED APODIZATION ALGORITHM TO DYNAMICALLY APODIZE THE DIGITAL CHANNEL DATA USING A SELECTED APODIZING FUNCTION h[n,k], WHERE n IS A SAMPLE NUMBER. THE INTEGRATED APODIZATION ALGORITHM COMPRISES (i) APPLYING DYNAMIC APERTURE CONTROL FOR CREATING AN EFFECTIVE APERTURE COMPRISING GENERATING A PARAMETER numApertureChannels (Nap[n]) WHERE Nap[n] IS ≤ Nac, AND SELECTING Nap[n] PARTICULAR ONES FROM THE PLURALITY OF DATA CHANNELS BASED ON A DYNAMIC BEAM FOCUSING LOCATION FOR THE BEAMFORMING, AND (ii) APPLYING DYNAMIC DATA SCALING TO PROVIDE DATA NORMALIZATION USING A VECTOR INNER PRODUCT RELATION BETWEEN THE APODIZING FUNCTION h[n,k] AND A SCALE FACTOR TO GENERATE NORMALIZED APODIZATION FACTORS $h_{norm}[n,k]$ 503 — APPLYING NORMALIZED APODIZATION FACTORS $h_{norm}[n,k]$ TO THE DIGITAL CHANNEL DATA TO GENERATE APODIZED AND NORMALIZED DIGITAL CHANNEL DATA FOR THE DATA CHANNELS DEFINED BY $N_{ap}[n]$ PARTICULAR ONES DURING AT LEAST ONE OF THE SAMPLES NUMBERS [n]

```
;*
;*------------------------------------------------------------------------
;*   SOFTWARE PIPELINE INFORMATION
;*
;*       Loop source line            : 164
;*       Loop opening brace source line   : 166
;*       Loop closing brace source line   : 319
;*       Known Minimum Trip Count         : 2
;*       Known Max Trip Count Factor      : 2
;*       Loop Carried Dependency Bound(^) : 9
;*       Unpartitioned Resource Bound     : 10
;*       Partitioned Resource Bound(*)    : 11
;*       Resource Partition:
;*                              A-side    B-side
;*       .L units                 1         2
;*       .S units                 4         8
;*       .D units                 2         1
;*       .M units                 5         9
;*       .X cross paths           1         7
;*       .T address paths         0         3
;*       Long read paths          0         0
;*       Long write paths         0         0
;*       Logical ops (.LS)        1        10      (.L or .S unit)
;*       Additional ops (.LSD)   16        10      (.L or .S or .D unit)
;*       Bound (.L .S .LS)        3        10
;*       Bound (.L .S .D .LS .LSD)   8     11*
;*
;*       Searching for software pipeline schedule at ...
;*          ii = 15 Schedule found with 5 iterations in parallel
```

*FIG. 6*

DYNAMIC APERTURE CONTROL AND NORMALIZATION FOR APODIZATION IN BEAMFORMING

CROSS REFERENCE TO RELATED APPLICATIONS

This application claims the benefit of Provisional Application Ser. No. 61/420,068 entitled "DYNAMIC APERTURE AND NORMALIZATION METHOD FOR APODIZATION IN ULTRASOUND BEAMFORM APPLICATIONS" filed Dec. 6, 2010, which is herein incorporated by reference in its entirety.

FIELD OF THE INVENTION

Disclosed embodiments relate to beamformers for ultrasound and related beamforming algorithms, and integrated circuits (ICs) implementing disclosed beamforming algorithms, and ultrasound systems therefrom.

BACKGROUND

Beamforming is a signal processing technique used in sensor arrays for directional signal transmission or reception. Spatial selectivity is achieved by using adaptive or fixed receive/transmit beam patterns.

One medical application that uses beamforming is ultrasound diagnostics. Ultrasound energy is focused at target tissue by a transmit beamformer, and ultrasound energy modulated and returned by the target tissue is focused by a receive beamformer. The receive beamformer may provide signals for generation of B-mode images, color Doppler or spectral Doppler information representing the target tissue, or combinations thereof. Such beamforming systems can provide real-time, cross-sectional (tomographic) 2D images of human body tissue, or the tissue of another subject.

In traditional ultrasound imaging systems, custom application-specific integrated circuit (ASIC) devices perform the beamformer computations. As part of the software beamforming solution, apodization which involves application of appropriate gains to each data channel (each including a dedicated transducer element) is needed to shape the incoming signals in each data channel. This shaping reduces the grating side lobe effects in the beamformed signal that stem from lateral pressure amplitude variations and transducer element spacing.

Other features are desirable in the signal processing data path including dynamic aperture control and data normalization. Dynamic aperture control functions to maintain a desired aperture over the entire ultrasound scanline by dynamically adjusting the number of active transducer elements. Regarding normalization, since a different number of transducer elements may be used at each sample number n (each sample number n corresponding to a different time instant), normalization can account for this scaling effect to maintain a constant signal level for the beamformed signal.

Figure 1:
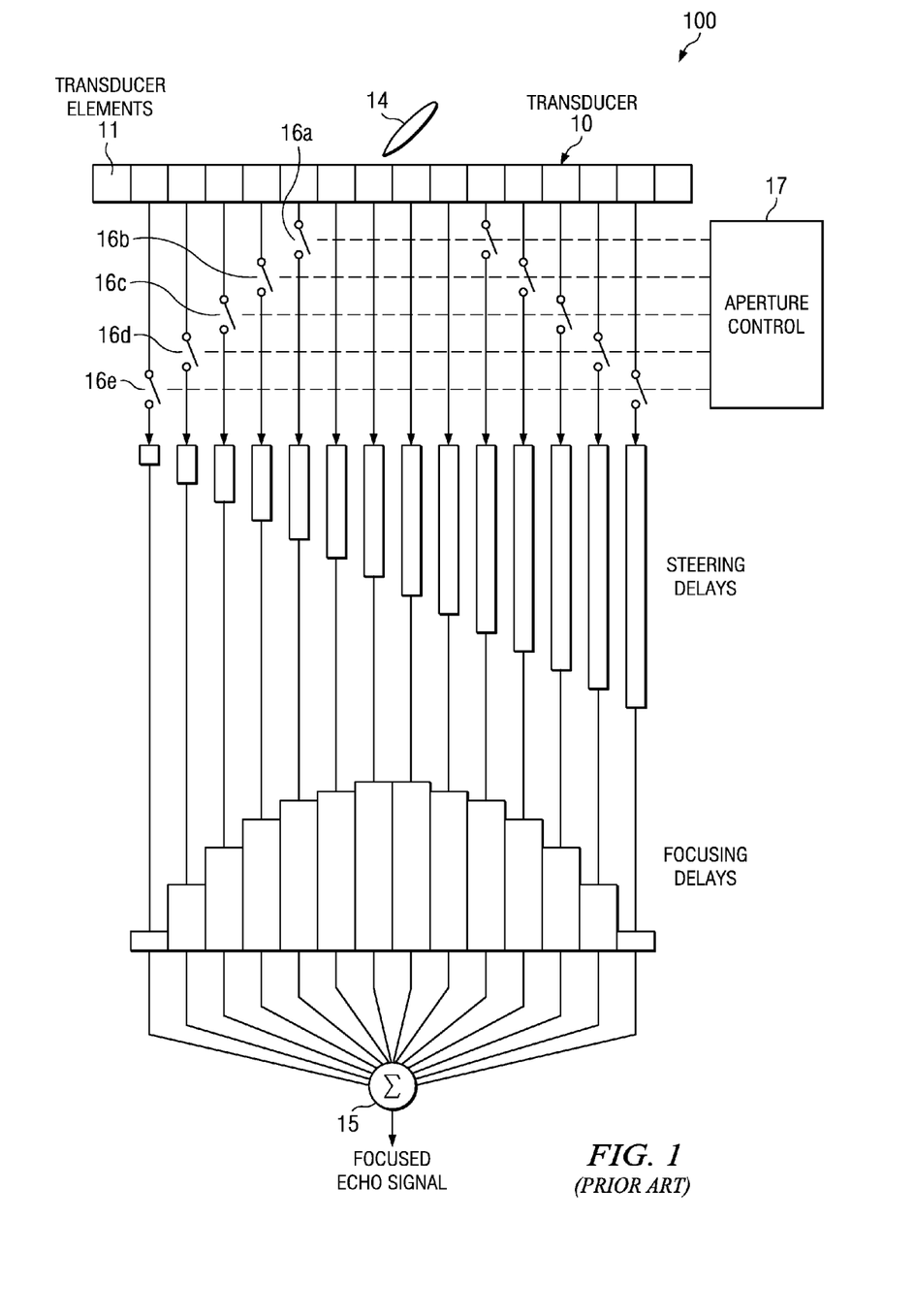
FIG. 1 schematically depicts a simplified block diagram depiction of a conventional ultrasound beamformer system for imaging target tissue that includes switch-based time delay steering and focusing of received echo signals from a receive array of transducer elements.

In most ASIC beamformer system designs, the aperture control is handled via analog switches that enable selection of specific combinations of channels of data as a function of a desired aperture. FIG. 1 schematically depicts a simplified block diagram depiction of a conventional ultrasound beamformer system 100 for imaging target tissue that includes switch-based time delay steering and focusing of received echo signals 14 from echoes returning from targets. System 100 comprises a receive array 10 comprising a plurality of transducer elements 11, shown configured as a linear array.

Dynamic aperture control is shown schematically in FIG. 1 as a plurality of pairs of receiver channel switches 16a-16e which are closed in sequence during the echo reception period by an aperture control circuit 17. Aperture control circuit 17 dynamically selects which of the transducer elements 11 are active transducer elements at any given sample time (instant). For each active transducer element 11 while in the receive mode a data channel is established to move target data from the transducer element 11 to signal processing elements in the beamformer. Receiving channel switches 16a-16e are analog electronic switches. Data channels are associated with each of the switches 16a, 16b, 16c, 16d and 16e.

The data from the respective active transducer elements 11 in each data channel is delayed by respective processing channel time delays comprising the steering delays and focusing delays shown in FIG. 1 during the echo reception period, which acts to dynamically focus the received signal echoes. Following application of the channel time delays, although not shown in FIG. 1, the respective delayed channel signals may be apodized so that each received channel signal is scaled by a desired value using an apodization factor to reduce the grating side lobe effects in the later formed beamformed signal as described above. The apodized signals are then summed by a summing amplifier 15 to produce a beamformed signal shown as a "focused echo signal" in FIG. 1. A plurality of focused echo signals can be used to form a scanline and a plurality of scanlines can be combined to form an image of the target tissue on a suitable display device.

Although not shown, the focused echo signal output by summing amplifier 15 can then optionally be normalized at each sample time n. Normalization can be used to keep the average signal level substantially the same (constant) over the entire scanline over the sample instants n.

The type of dynamic aperture control implemented by conventional ultrasound beamformer system 100 can be difficult to synchronize in terms of the number of active channels and sample time, especially if the implementation is analog. As a result of this synchronization difficulty, determining the data normalization needed to keep the average signal level the same (constant) along the entire scanline as a function of sample time generally becomes even more problematic.

SUMMARY

Disclosed methods include methods of apodization for ultrasound beamforming, ultrasound imaging systems therefrom, and hardware such as digital signal processors (DSPs) for implementing ultrasound imaging blocks and functions including the filter block, apodization block, dynamic aperture control block, controller, and summer. Digital channel data representing echo data from target tissue in a plurality (k) of data channels and a predefined number ($\leq k$) of active channels ($N_{act}$) selected from the plurality of data channels are provided.

A software-based integrated apodization algorithm dynamically apodizes the digital channel data using a selected apodizing function $h[n,k]$. The integrated apodization algorithm applies dynamic aperture control to create an effective aperture by generating a parameter numApertureChannels ($N_{ap}[n]$), where $N_{ap}[n]$ is $\leq N_{act}$, and selecting $N_{ap}[n]$ particular ones of the data channels based on a dynamic beam focusing location for ultrasound beamforming. Applied dynamic data scaling provides data normalization using a vector inner product between $h[n,k]$ and a scale factor to generate the normalized apodization factors $h_{norm}[n,k]$.

The normalized apodization factors can be applied to the digital channel data only in the $N_{ap}[n]$ particular data channels to generate apodized and normalized digital channel data. Filtering is also applied to the channel data in the $N_{ap}[n]$ particular data channels, either before or after dynamic apodization. Because apodization and filtering can only be applied to data in the $N_{ap}[n]$ particular data channels used to form the aperture at each sample number n (time instant), data processing efficiency is significantly increased (e.g., less cycles) as opposed to arrangements that apodize and filter data from all the data channels in the system.

Disclosed embodiments solve the unmet need for an integrated apodization methodology by providing a software-based approach which performs both dynamic aperture control and normalization to produce scaled beamformed data for ultrasound beamformer systems. Disclosed embodiments enable apodization without switching of data channels since the normalization/scaling is handled using vector inner products, thus avoiding the need to switch between data channels.

A more timing accurate integrated apodization algorithm is provided in part because the relationship between the aperture channels and data normalization is known at each sample number (n). Being software based, disclosed integrated apodization algorithms can be used for any desired apodization function. Disclosed integrated apodization methodologies also are efficient to implement in hardware as they involve fewer cycles to produce an equivalent numerical result (as compared to conventional algorithms which are significantly more multiplier intensive). Disclosed integrated apodization algorithms can be used to perform data normalization for a given (single) scanline, or for all of the scanlines in an entire ultrasound image.

DETAILED DESCRIPTION

Disclosed embodiments will be described more fully hereinafter with reference to the accompanying drawings. This Disclosure may, however, be embodied in many different forms and should not be construed as limited to the embodiments set forth herein. Rather, these embodiments are provided so that this Disclosure will be thorough and complete, and will fully convey the scope of the disclosed subject matter to those having ordinary skilled in the art. One having ordinary skilled in the art may be able to use the various embodiments disclosed herein.

As described above, conventional ultrasound systems such as conventional ultrasound beamformer system 100 shown in FIG. 1 perform dynamic aperture control using analog channel switches, apodization of the channel data (if implemented), and normalization of summed channel data (if implemented) for the scaling the average signal level to be the same (constant) of the entire scanline in separate locations (e.g., as separate data processing blocks) within the beamformer system. Some parts of the signal processing may be performed in analog (e.g., aperture control 17) and some portions performed in digital (the apodization if implemented). In contrast, disclosed integrated apodization methodologies provide a software-based approach which performs dynamic aperture control and normalization thus combining previously separate data processing operations into a single operation to ensure the scaling accuracy of the data, which also eliminates the need for switches.

Disclosed software-based integrated apodization algorithms are implementable on ICs such as ASICs, field-programmable gate array (FPGAs) and DSPs. Since as described below the scaling is handled with vector inner products, the need for switches is eliminated. Also, since the relationship between the respective data channels used for dynamic aperture normalization are known at each sample number n (time instant), the data can be accurately scaled at each sample number n.

To more accurately and deterministically implement both dynamic aperture control and data normalization, an example software-based integrated apodization method is disclosed below. In general, a discrete-time implementation of the apodization process can be expressed mathematically as:

$$y[n,k] = h[n,k] * x[n,k] \tag{1}$$

where $h[n,k]$ is the apodization function for the $k^{th}$ data channel for sample number n, $x[n,k]$ is the signal received from the $k^{th}$ data channel at sample number n, and $y[n,k]$ is the filtered receive signal from the $k^{th}$ data channel at sample number n. For the simple unity gain apodization functions $h[n,k]$, the apodization function $h[n,k]$ can be defined as:

$$h[n,k] = \begin{cases} 0 & \text{for } k \notin K_{ap}[n], n \geq 0 \\ 1 & \text{for } k \in K_{ap}[n], n \geq 0 \end{cases} \tag{2}$$

where $K_{ap}[n]$ defines the set of aperture channel indices as a function of sample number n, where each n corresponds to a particular time instant. For more complicated apodization functions $h[n,k]$, such an the specific Gaussian windowing function referred to in the art as a Hanning window, the apodization function becomes the following representation:

$$h[n,k] = \begin{cases} 0 & \text{for } k \notin K_{ap}[n], n \geq 0 \\ \frac{1}{2}\left(1 - \cos\left(\frac{2\pi(k+1)}{N_{ap}[n]+1}\right)\right) & \text{for } k \in K_{ap}[n], n \geq 0 \end{cases} \tag{3}$$

where cos( ) is the cosine function and $N_{ap}[n]$ defines the number (N) of aperture channels (active data channels) as a function of sample number n.

To determine the number of aperture channels active at a given sample number n (time instant), referred to herein as $N_{act}$, the f# (i.e. f number) for the aperture is defined in terms of the transducer parameters. $N_{act}$ is generally user specified and involves selection of a maximum number of data channels (each associated with a transducer) to be utilized for beamforming, where $N_{act}$ is ≤the number of data channels/transducer elements in the beamforming system. In optics, the $f_\#$ is defined as the ratio of the focal point distance of the lens ($R_{fp}$) to the diameter (D) of the lens, which can be written mathematically as:

$$f_\# = \frac{R_{fp}}{D} \quad (4)$$

In most applications, good focusing is achieved when the $f_\#$ is equal to one. However, disclosed embodiments include $f_\#$s not equal to one.

The $f_\#$ can be express in terms of ultrasound transducer parameters as:

$$f_\# = \frac{R_{fp}}{N_{ap}[n] * elemPitch} \quad (5)$$

where $R_{fp}$ is the radial distance to the lens focal point and elemPitch is the spacing between the respective transducer elements. Equation (5) can be written to account for non-constant element pitch with increased complexity. Since the objective of the beamformer is to dynamically adjust the focal point at each sample number n of the discrete-time system, the focal point distance to the lens $R_{fp}$ can be written as $$R_{fp} = \frac{c}{2 \cdot f_s} \cdot n \quad (6)$$

where c is the speed of sound in the tissue of interest and $f_s$ is the sampling rate of the discrete-time signal processing system. Substituting Equation (6) into Equation (5), the following relationship is derived that describes the number of data channels $N_{ap}[n]$, which defines the number of aperture channels, selected from the active channels $N_{act}$ needed to create the desired aperture at a given sample number n to achieve good focusing.

$$N_{ap}[n] = \frac{c}{2 \cdot f_s \cdot f_\# \cdot elemPitch} \cdot n \quad (7)$$

Equation (7) for $N_{ap}[n]$ enables the determination of the set of indices (i.e. $K_{ap}[n]$) needed to create the aperture at each sample number n so that the selected apodization function, such as a Gaussian windowing function such as Hanning or Hamming apodization window, can be applied only to the Nap [n] particular ones of the datachannels, thus saving data processing resources. $K_{ap}[n]$ is shown in Equation 2 above.

For example, the beam focusing location for phased array transducers is located in the middle (midpoint) of the transducer elements making up the transducer. As a result, the desired aperture is created by using $N_{ap}[n]$ channels centered about the middle of the transducer. However, for linear array transducers, the beam focusing location for linear array transducers is moved along the face of the transducer. As a result, the desired aperture is created by using $N_{ap}[n]$ channels about the dynamic beam focusing location.

Once apodization has been applied to the channel data, the apodized channel data can be normalized to keep the average signal level the same (effectively constant) along the entire scanline over the sample numbers n. The scale factor $K_{rat}[n]$ to achieve normalization is referred to herein as a normalization scale factor $K_{rat}[n]$ that can be written as:

$$K_{rat}[n] = \frac{N_{act}}{N_{ap}[n]} \quad (8)$$

where as described above $N_{act}$ is the number of active transducer channels. It is noted that a value for the maximum value of this scale factor $K_{rat}[n]$ should be specified to handle the 1 divided by 0 case and to handle the normalization for all of the scanlines in a given ultrasound image. Thus, the range of possible values for the normalization scale factor $K_{rat}[n]$ can be expressed as:

$$1 \le K_{rat}[n] \le K_{max} \quad (9)$$

Using this normalization scale factor $K_{rat}[n]$ in (8,9) and the relationship for the number of aperture channels $N_{ap}[n]$ in (7), the following general inner product relationship shown below as (10) can be generated and used to compute the normalized apodization implementation $h_{norm}[n,k]$ for any selected apodization function h[n,k]:

$$h_{norm}[n,k] = K_{rat}[n] \cdot h[n,k] \text{ for } 0 \le k \le N \quad (10)$$

where h[n,k] is the desired apodization function and $h_{norm}[n,k]$ is the normalized version of the desired apodization function.

Figure 2:
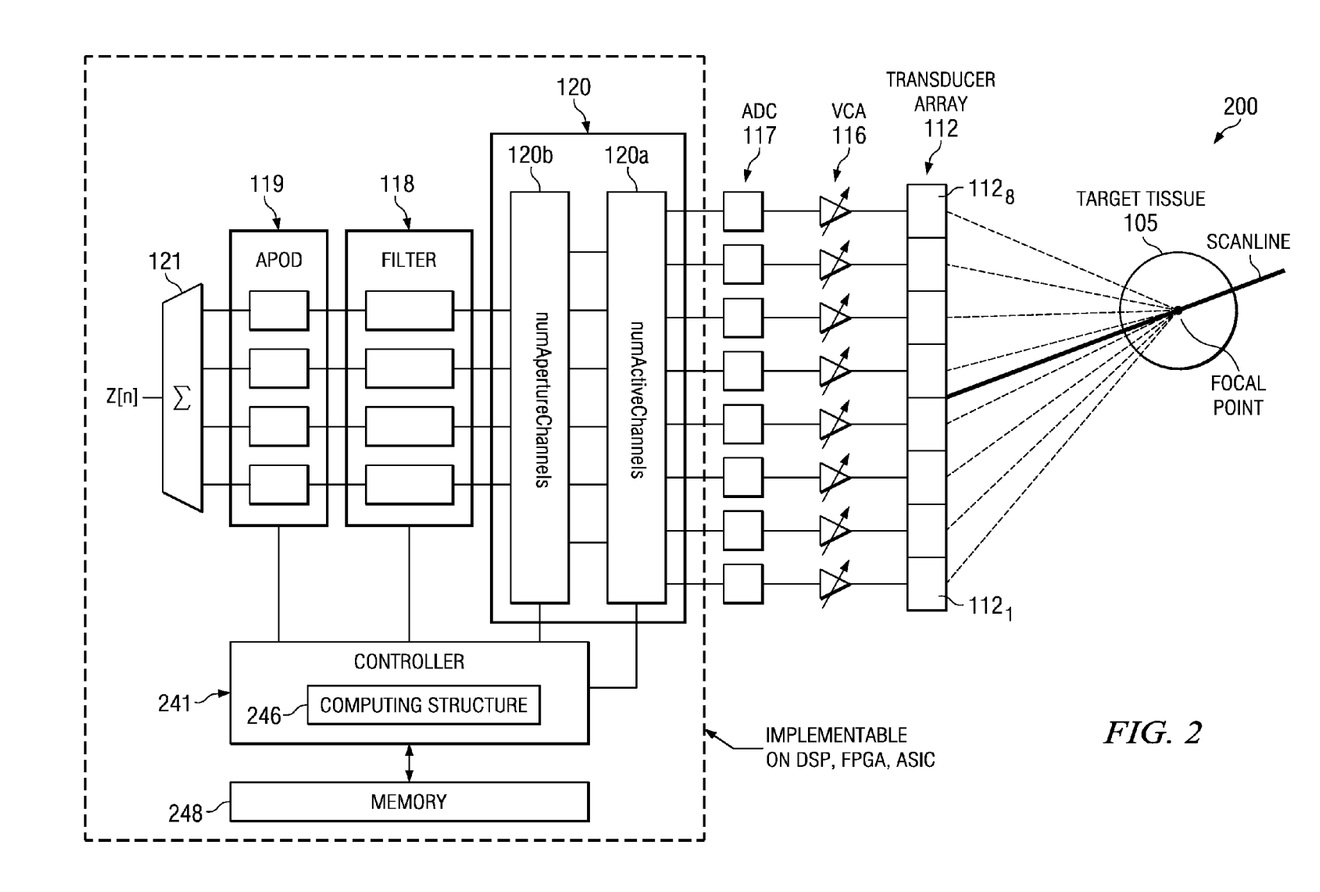
FIG. 2 schematically depicts a simplified block diagram depiction of a ultrasound beamformer system for imaging target tissue that includes disclosed dynamic aperture control and normalization, according to an example embodiment.

FIG. 2 schematically depicts a simplified block diagram depiction of a ultrasound beamformer system 200 for imaging target tissue that includes disclosed dynamic aperture control and normalization, according to an example embodiment. In a typical embodiment, beamformer system 200 is a delay and sum ultrasound beamformer system.

Although FIG. 2 is shown with transducer elements arranged in a linear fashion, as in some phased array scanning systems, disclosed embodiments may also be used for transducer elements positioned in other configurations such as curved, cylindrical, as well as 2-D (i.e. two dimensional) and 3-D (i.e. three dimensional) arrangements. Moreover, disclosed embodiments are also applicable to other types of array transducers, including curvilinear or curved transducers, cylindrical transducers, annular array transducers, and rectangular array transducers.

Beamformer system 200 comprises a transducer array 112 comprising a plurality (k) of transducer elements shown as elements $112_1$-$112_8$ that each define data channels which comprise piezoelectric transducers that convert sound waves echoed by the target tissue 105 into electrical sensing signals. Transducer elements $112_1$-$112_8$ thus form the first element in the eight (8) separate data channels 1 through 8 (one transducer per data channel) that extend from the transducer elements $112_1$-$112_8$ to the numActiveChannels ($N_{act}$ block 120a as described below.

The respective transducers in transducer array 112 are each coupled to a voltage-controlled amplifier (VCA) 116, then to an analog to digital converter (ADC) 117 for digital conversion of the amplified transducer signal. The ADCs 117 in FIG. 2 are coupled to block 120a shown as $N_{act}$ of dynamic aperture control block 120 shown controlled by the controller 241 shown. $N_{act}$ sets the maximum number of the k data channels that are used by the beamformer system 200, which is gener ally predefined and held constant, such as provided by user input and stored in memory. $N_{act}$ has the following constraint:

$$0 \le N_{act} \le numChannels (numChannels=8 \text{ as shown in FIG. 2})$$

$N_{act}$ block 120a is shown in FIG. 2 in the example where six (6) out of the possible eight (8) data channels shown in FIG. 2 are selected. Dynamic aperture control block 120 also comprises numApertureChannels ($N_{ap}$) computation block 120b. The dynamic $N_{ap}[n]$ computation as disclosed above is shown implemented by $N_{ap}$ computation block 120b under control by controller 241. $N_{ap}[n]$ computation block 120b is operable to dynamically determine the particular data channels used to create an effective aperture.

$N_{ap}[n]$ has the following constraint:

$$0 \le N_{ap} \le N_{act}$$

The outputs provided by $N_{ap}$ computation block 120b are coupled to filter block 118 comprising a plurality of filters which apply appropriate time delays to compensate for different echo arrival times due to path length differences between the target tissue 105 and the respective transducer elements $112_1$-$112_8$. The filters in filter block 118 are coupled to apodization blocks in apodization gain block 119 which generate apodized and normalized channel data for data in the $N_{ap}[n]$ particular ones from the plurality of data channels selected based on a dynamic beam focusing location for the beamforming. Apodization gain block 119 thus provides scaling (i.e. weighting) the respective data channel signals provided. The apodization gains provided by the apodization gain blocks 119 to the respective $N_{ap}[n]$ particular data channels are based on the normalized version of the desired apodization function $h_{norm}[n,k]$ as described above, which are thus changed on a sample-by-sample (n-by-n) basis.

The outputs of the respective apodization gain blocks 119 are coupled to an adder 121 that sums the apodized and normalized signals output by apodization gain block 119 to generate the desired beamformed signal shown as z[n] which represents the focused and normalized echo signal. A plurality of focused and normalized echo signals z[n] can be used to form a scanline, and a plurality of scanlines can be combined to form an image of the target tissue 105 on a suitable display device.

System 200 also includes a controller 241 that comprises a computing structure 246. Controller 241 can be provided by devices including one or more DSPs, FPGAs or ASICs. For example, a DSP can provide all components of system 200 within the dashed line shown in FIG. 2. System 200 includes memory 248 for storing data including disclosed integrated apodization algorithms and sample count (number) data during beamforming, that is coupled to controller 241. Controller 241 is operable to load data from memory 248 for processing.

Controller 241 can be seen to be coupled to control both filter block 118 and apodization block 119. The weighting factors provided to the respective data channels in apodization gain blocks 119 are based on the normalized apodization implementation $h_{norm}[n,k]$ for the selected apodization function h[n,k] noted above as (10), copied again below:

$$h_{norm}[n,k] = K_{rat}[n] \cdot h[n,k] \text{ for } 0 \le k \le N \qquad (10)$$

where h[n,k] is the desired apodization function and $h_{norm}[n,k]$ is the normalized version of the desired apodization function.

Figure 3:
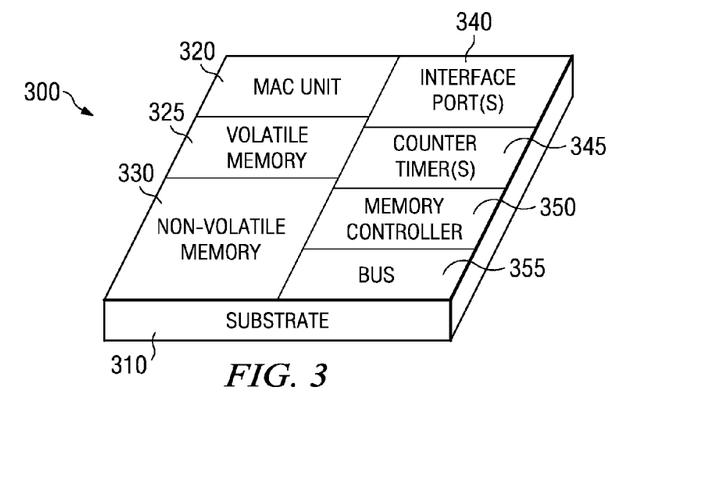
FIG. 3 shows a simplified block diagram of a DSP IC according to an embodiment of the invention that can implement all the system elements within the dashed line shown in FIG. 2.

FIG. 3 shows a simplified block diagram of a DSP IC 300 according to an example embodiment that can implement all the system elements within the dashed line shown in FIG. 2. DSP IC 300 is shown formed on a substrate 310 having a top semiconductor surface (e.g., a silicon substrate) and comprises a multiply-accumulate (MAC) unit 320 that is operable to generate control signals to implement disclosed dynamic aperture control and normalization. DSP IC 300 generally includes a volatile memory (e.g., RAM) 325 and non-volatile memory (e.g., ROM) 330. Algorithms according to embodiments of the invention can be stored in non-volatile memory 330. The DSP IC 300 is also shown including interface port(s) 340 for inputs and outputs, counter/timers 345, memory controller 350 and bus 355.

As with conventional DSPs, the DSP IC 300 can execute instructions to implement one or more digital signal processing algorithms or processes. For instance, the instructions data can include various coefficients and instructions that, when loaded and initialized into DSP IC 300, can prompt the DSP IC 300 to implement different digital signal processing algorithms or processes. The DSP IC 300 can receive data from ADC's 117 shown in FIG. 2 and then apply algorithms to the data according to its current configuration.

MAC unit 320 generally includes delaying and apodizing circuitry for processing digitized ultrasound sensing signals to form delayed, apodized and normalized digital ultrasound sensing signals. MAC unit 320 unit can also provide the controller 241 and computing structure 246. Volatile memory 325 can provide any memory needed.

Figure 4:
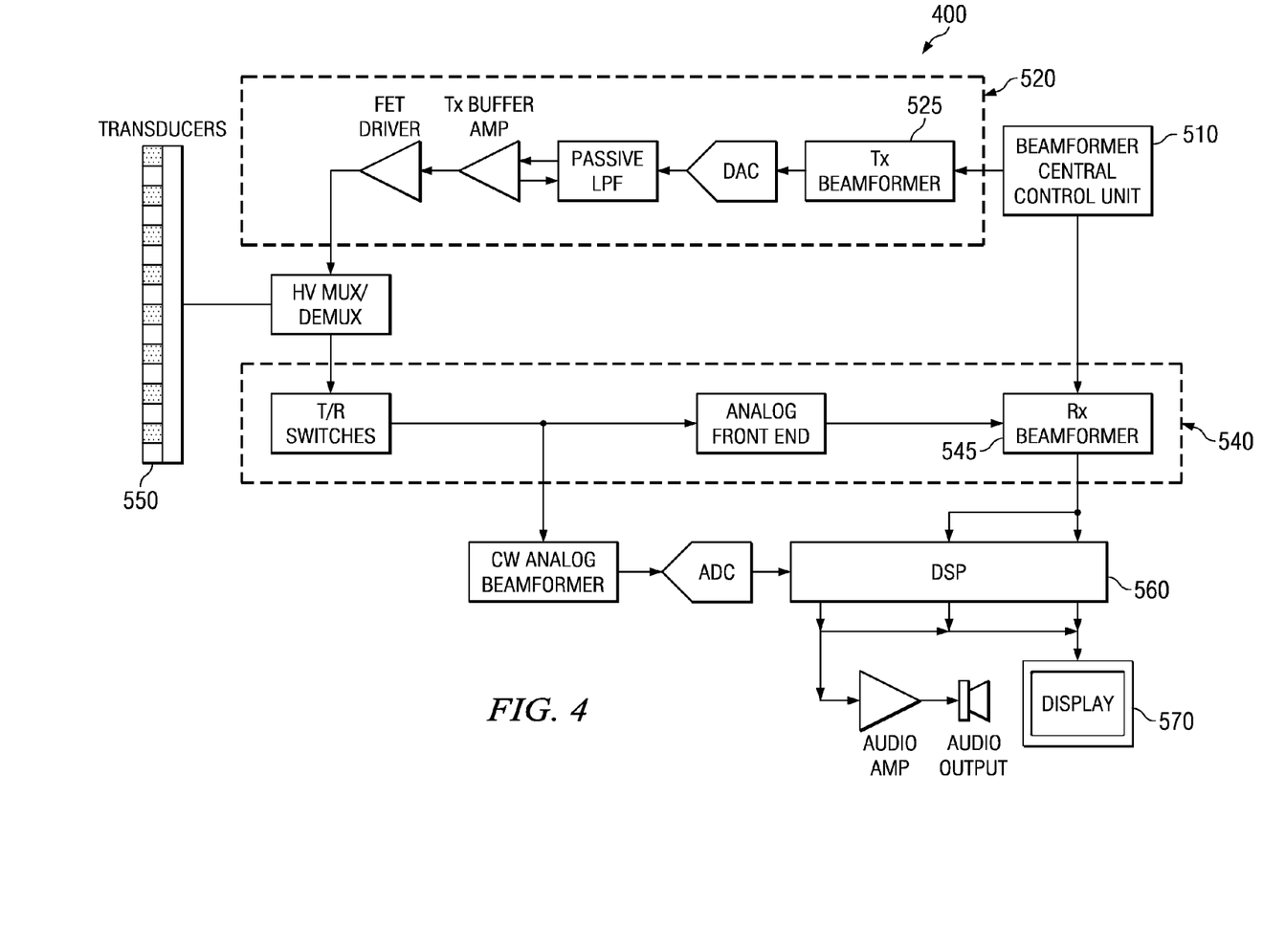
FIG. 4 is a block diagram of an exemplary ultrasound system that can implement disclosed dynamic aperture control and normalization, according to an example embodiment.

FIG. 4 is a block diagram of an exemplary ultrasound system 400 that can implement disclosed dynamic aperture control and normalization according to an example embodiment. System 400 includes a transmit section 520 comprising transmit (Tx) beamformer 525 and a receive section 540 comprising receive (Rx) beamformer 545 that share a common array of transducers 550.

System 400 includes a beamformer central control unit 510 that is coupled to both Tx beamformer 525 and Rx beamformer 545. Beamformer central control unit 510 can be embodied as a DSP, such as DSP IC 300 described above relative to FIG. 3, for implementing disclosed dynamic aperture control and normalization described above provided by the ultrasound beamformer system 200 shown in FIG. 2. Rx beamformer 545 of receive section 540 is coupled to a back-end imaging DSP 560. Backend imaging DSP 560 is coupled to a display 570.

Figure 5:
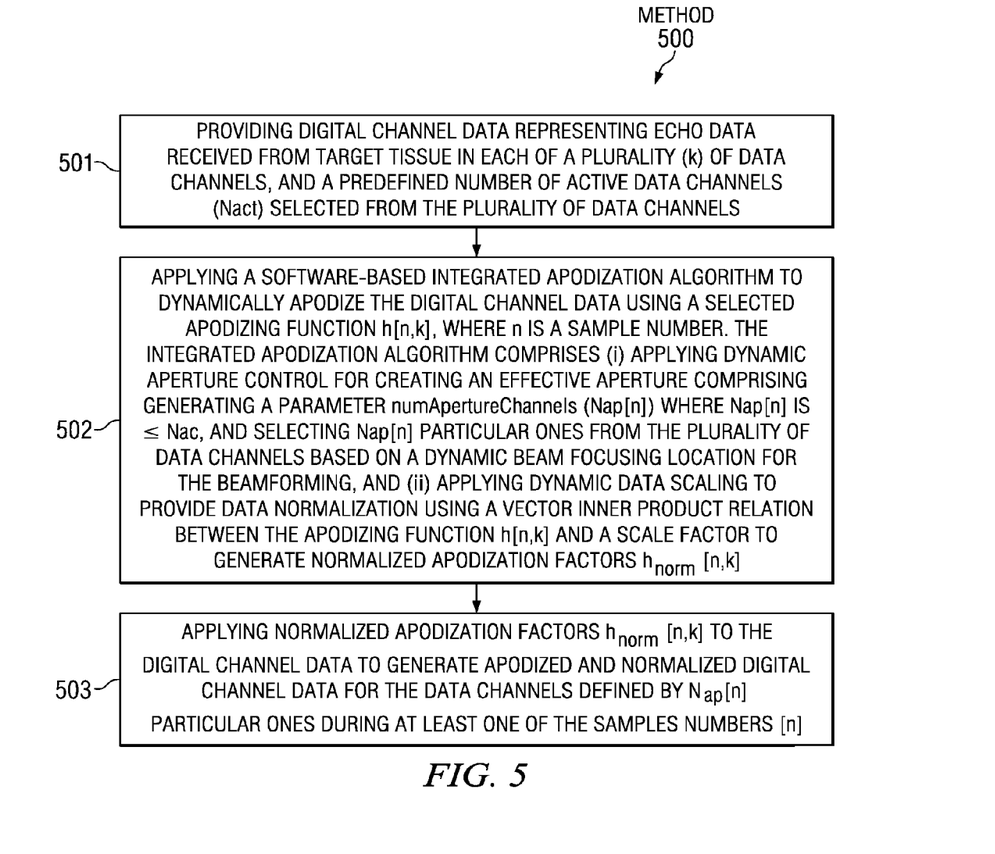
FIG. 5 is a flow chart for a method of apodizing ultrasound signals including dynamic aperture control and normalization, according to an example embodiment.

FIG. 5 is a flow chart for a method 500 of apodizing ultrasound signals received from a plurality of data channels (k) each associated with different ones of a plurality of transducer elements for ultrasound beamforming, according to an example embodiment. Step 501 comprises providing digital channel data representing echo data received from target tissue in each of the plurality of data channels, and a predefined number of active data channels ($N_{act}$) from the plurality of data channels.

Step 502 comprises applying a software-based integrated apodization algorithm to dynamically apodize the digital channel data using a selected apodizing function h[n,k], where n is a sample number, with a computing system (such as controller 241 including computing structure 246 shown in FIG. 2) including non-transitory machine readable storage (such as memory 248 shown in FIG. 2) to implement a disclosed integrated apodization algorithm. The integrated apodization algorithm comprises (i) applying dynamic aperture control for creating an effective aperture comprising generating a parameter numApertureChannels ($N_{ap}[n]$) where $N_{ap}[n]$ is $\le N_{act}$, selecting $N_{ap}[n]$ particular ones from the plurality of data channels based on a dynamic beam focusing location for the beamforming, and (ii) applying dynamic data scaling to provide data normalization using a vector inner product relation between the apodizing function h[n,k] and a scale factor to generate normalized apodization factors $h_{norm}[n,k]$.

Step 503 comprises applying normalized apodization factors $h_{norm}[n,k]$ to the digital channel data to generate apodized and normalized digital channel data for the data channels defined by the $N_{ap}[n]$ particular ones during at least one of the sample numbers [n]. Method 500 also comprises filtering which applies appropriate time delays to the respective data channels to compensate for different echo arrival times. Filtering can be implemented before or after apodizing in the data processing flow. Although mathematically filtering can follow apodizing, in practice filtering following apodizing will result in apodizing more data values (e.g., requiring more multiplications) as compared to the data processing flow where filtering precedes apodizing (such as shown in system 200 in FIG. 2). Apodized and normalized filtered digital channel data from the $N_{ap}[n]$ particular data channels selected based on the dynamic beam focusing location for the beamforming can then be used to generate the desired beamformed signal (shown as z[n] in FIG. 2) which represents the focused and normalized echo signal.

Figure 6:
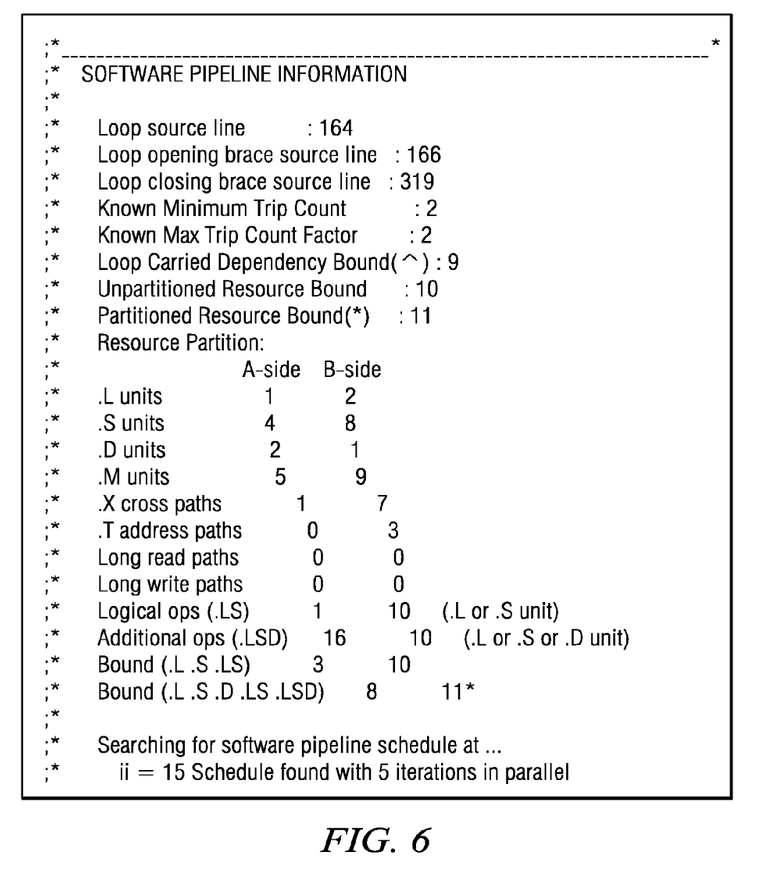
FIG. 6 provides software pipeline information for an integrated apodization algorithm based on a Hanning window running on C64+ of an architecture of a Texas Instruments Incorporated DSP, according to an example embodiment.

A disclosed integrated apodization algorithm which includes dynamic aperture control and normalization has been implemented in C code and demonstrated on a TMS320C6474 DSP manufactured by Texas Instruments Incorporated. Hanning apodization was implemented in software targeted for the TI DSP C64+ architecture. The software pipeline information for the integrated apodization algorithm ran on the C64+ architecture is shown in FIG. 6.

The particular integrated apodization algorithm was found to take 15 cycles to compute each apodization value for implementing both dynamic aperture control and normalization. It is noted that the architecture involved implementing disclosed integrated apodization algorithms is not multiplier (M unit) limited, but is instead shift/load (L, S, D unit) limited. The advantage of being L, S, D unit limited is that the data processing is less data intensive. Disclosed algorithms can be supported by apodization tables computed offline and stored in a table and referenced to reduce the pipelined schedule to the ideal bound of 11 cycles shown.

Those skilled in the art to which this disclosure relates will appreciate that many other embodiments and variations of embodiments are possible within the scope of the claimed invention, and further additions, deletions, substitutions and modifications may be made to the described embodiments without departing from the scope of this disclosure. For example, disclosed dynamic aperture control (as normalization is not needed for transmit beamforming) may be used for transmit ultrasound beamforming. Moreover, disclosed beamforming may be extended beyond ultrasound applications.

The invention claimed is:

1. A method of apodizing ultrasound signals received from a plurality of data channels (k) each associated with different ones of a plurality of transducer elements for ultrasound beamforming, comprising:
providing digital channel data representing echo data received from target tissue in each of said plurality of data channels and a predefined number of active data channels ($N_{act}$) selected from said plurality of data channels;
applying a software-based integrated apodization algorithm to dynamically apodize said digital channel data using a selected apodizing function h[n,k], where n is a sample number, using a computing system including non-transitory machine readable storage to implement said integrated apodization algorithm, said integrated apodization algorithm comprising:
  (i) applying dynamic aperture control for creating an effective aperture comprising generating a parameter numApertureChannels ($N_{ap}[n]$) where $N_{ap}[n]$ is $\leq$ said $N_{act}$, and selecting $N_{ap}[n]$ particular ones from said plurality of data channels based on a dynamic beam focusing location for said ultrasound beamforming;
  (ii) applying dynamic data scaling to provide data normalization using a vector inner product relation between said apodizing function h[n,k] and a scale factor to generate normalized apodization factors $h_{norm}[n,k]$, and
applying said normalized apodization factors $h_{norm}[n,k]$ to said digital channel data to generate apodized and normalized digital channel data for said data channels defined by said $N_{ap}[n]$ particular ones during at least one of said [n],
wherein said scale factor is represented by $K_{rat}[n]$ and said vector inner product relation comprises:

$$h_{norm}[n,k] = K_{rat}[n] \cdot h[n,k] \text{ for } 0 \leq k \leq N, \text{ wherein}$$

$$K_{rat}[n] = \frac{N_{act}}{N_{ap}[n]}.$$

2. The method of claim 1, wherein said normalized apodization factors hnorm [n,k] are exclusively only provided to said Nap[n] particular ones of said plurality of data channels.

3. The method of claim 1, wherein said selected apodizing function h[n,k] comprises a Gaussian windowing function.

4. The method of claim 2, further comprising:
filtering said digital channel data exclusively only for said $N_{ap}[n]$ particular ones of said plurality of data channels so that said apodized and normalized digital channel data comprises apodized and normalized filtered digital channel data;
summing said apodized and normalized filtered digital channel data to produce a beamformed signal;
changing said dynamic beam focusing location along a line;
repeating said method including said summing and said changing a plurality of times to generate a plurality of said beamformed signals, and
generating a scanline from said plurality of beamformed signals.

5. The method of claim 4, further comprising:
generating a plurality of said scanlines, and
combining said plurality of said scanlines to form an image of said target tissue on a display device.

6. The method of claim 1, further comprising using a digital signal processor (DSP) for filtering said digital channel data exclusively only for said $N_{ap}[n]$ particular ones of said plurality of data channels so that said apodized and normalized digital channel data comprises apodized and normalized filtered digital channel data, and for applying said software-based integrated apodization algorithm to dynamically apodize said filtered digital channel data.

7. An ultrasound imaging system for ultrasound beamforming, comprising:
a plurality (k) of transducer elements for transmitting ultrasound transmit pulses toward a target tissue, and receiving echo signals from said target tissue in response;

a transmit section for driving said plurality of transducer elements for said transmitting of said ultrasound transmit pulses, and a receive section for processing a plurality of sensing signals generated by said plurality of transducers responsive to said echo signals, said receive section defining a plurality of data channels each associated with different ones of said plurality of transducer elements, said receive section comprising:

a digitizing block for generating digital channel data representing echo data from said echo signals in each of said plurality of data channels, a dynamic aperture control block coupled to an output of said digitizing block comprising a $N_{act}$ block for setting a number of said plurality of data channels used by said system and a dynamic numApertureChannels ($N_{ap}[n]$) computation block for dynamically determining a number $N_{ap}[n]$ of said plurality of data channels to create an effective aperture;

a filter block coupled to an output of said $N_{ap}[n]$ computation block for filtering said digital channel data to generate filtered digital channel data, an apodization block coupled to said filter block;

a controller and associated memory coupled to control said filter block, said apodization block, and said dynamic aperture control block;

wherein said controller executes a software-based integrated apodization algorithm for dynamically apodizing said filtered digital channel data using a selected apodizing function $h[n,k]$, where n is a sample number, with a computing system to implement said integrated apodization algorithm including non-transitory machine readable storage, said integrated apodization algorithm comprising:

(i) dynamic aperture control for controlling said dynamic aperture control block to create said effective aperture including selecting $N_{ap}[n]$ particular ones from said plurality of data channels based on a dynamic beam focusing location for said beamforming, and (ii) dynamic data scaling to provide data normalization using a vector inner product relation between said apodizing function $h[n,k]$ and a scale factor $h_{norm}[n]$ to generate normalized apodization factors $h_{norm}[n,k]$;

wherein said controller provides said normalized apodization factors $h_{norm}[n,k]$ to said apodization block to process said filtered digital channel data to generate apodized and normalized filtered digital channel data during at least one of said [n];

a summer for summing coupled to outputs of said apodization block to form a beamformed signal;

a backend imaging display processor coupled to receive and process said beamformed signal to generate a display signal, said display signal being suitable for causing display devices to produce an image, and a display device for receiving said display signal and producing said image, wherein said scale factor is represented by $K_{rat}[n]$ and said vector inner product relation comprises:

$$h_{norm}[n,k] = K_{rat}[n] \cdot h[n,k] \text{ for } 0 \leq k \leq N, \text{ wherein}$$

$$K_{rat}[n] = \frac{N_{act}}{N_{ap}[n]}.$$

8. The ultrasound imaging system of claim 7, wherein said normalized apodization factors hnorm [n,k] are exclusively only provided to said Nap[n] particular ones of said plurality of data channels.

9. The ultrasound imaging system of claim 7, wherein said system is operable for:

changing said dynamic beam focusing location along a line, and repeating said summing and said changing a plurality of times to generate a plurality of said beamformed signals.

10. The ultrasound imaging system of claim 7, further comprising using a digital signal processor (DSP) for implementing said filter block, said apodization block, said dynamic aperture control block, said controller, and said summer.

11. A digital signal processor (DSP) integrated circuit (IC) for ultrasound signal processing, comprising:

a substrate having a semiconductor surface;

a dynamic aperture control block coupled to an output of a digitizing block that provides digital channel data representing echo data from echo signals in each of a plurality of data channels each associated with different ones of a plurality of transducer elements;

said dynamic aperture control block comprising a $N_{act}$ block for setting a maximum number of said plurality of data channels used and a dynamic numApertureChannels ($N_{ap}[n]$) computation block for dynamically determining a number $N_{ap}[n]$ of said plurality of data channels to create an effective aperture;

a filter block coupled to an output of said $N_{ap}[n]$ computation block for filtering said digital channel data to generate filtered digital channel data;

an apodization block coupled to said filter block;

a controller and associated memory coupled to control said filter block, said apodization block, and said dynamic aperture control and normalization block;

wherein said controller executes a software-based integrated apodization algorithm for dynamically apodizing said filtered digital channel data using a selected apodizing function $h[n,k]$, where n is a sample number, implementing said integrated apodization algorithm comprising:

(i) dynamic aperture control for controlling said dynamic aperture control and normalization block to create said effective aperture including selecting $N_{ap}[n]$ particular ones from said plurality of data channels based on a dynamic beam focusing location for said beamforming, and (ii) dynamic data scaling to provide data normalization using a vector inner product relation between said apodizing function $h[n,k]$ and a scale factor $K_{rat}[n]$ to generate normalized apodization factors $h_{norm}[n,k]$;

wherein said controller provides said normalized apodization factors $h_{norm}[n,k]$ to said apodization block to process said filtered digital channel data to generate apodized and normalized filtered digital channel data during at least one of said [n], and a summer for summing coupled to outputs of said apodization block to form a beamformed signal,
wherein said scale factor is represented by $K_{rat}[n]$ and said vector inner product relation comprises:

$h_{norm}[n,k] = K_{rat}[n] \cdot h[n,k]$ for $0 \le k \le N$, wherein $$K_{rat}[n] = \frac{N_{act}}{N_{ap}[n]}.$$

12. The DSP IC of claim 11, wherein said normalized apodization factors hnorm [n,k] are exclusively only provided to said Nap[n] particular ones of said plurality of data channels.

13. The DSP IC of claim 11, wherein said selected apodizing function h[n,k] comprises a Gaussian windowing function.

* * * * *